(12) United States Patent
Quaggin (10) Patent No.: US 9,629,348 B2
(45) Date of Patent: Apr. 25, 2017

(54) VECTOR CONSTRUCT WITH HUMAN HYPOXIA INDUCIBLE FACTOR α GENE

(71) Applicant: Mannin Research Inc., Toronto (CA)

(72) Inventor: Susan E. Quaggin, Chicago, IL (US)

(73) Assignee: MANNIN RESEARCH INC., Toronto (CA)

( * ) Notice: Subject to any disclaimer, the term of this patent is extended or adjusted under 35 U.S.C. 154(b) by 0 days.

(21) Appl. No.: 14/715,343

(22) Filed: May 18, 2015

(65) Prior Publication Data

US 2016/0015012 A1 Jan. 21, 2016

Related U.S. Application Data

(60) Provisional application No. 61/994,657, filed on May 16, 2014.

(51) Int. Cl.

| | |
|---|---|
| *C07H 21/02* | (2006.01) |
| *C12N 5/00* | (2006.01) |
| *C12N 15/00* | (2006.01) |
| *A01K 67/027* | (2006.01) |
| *A61K 49/00* | (2006.01) |
| *C07K 14/47* | (2006.01) |
| *C12N 15/85* | (2006.01) |

(52) U.S. Cl.
CPC ...... *A01K 67/0278* (2013.01); *A61K 49/0008* (2013.01); *C07K 14/4702* (2013.01); *C12N 15/8509* (2013.01); *A01K 2267/03* (2013.01); *C12N 2830/002* (2013.01); *C12N 2830/003* (2013.01)

(58) Field of Classification Search
None
See application file for complete search history.

(56) References Cited

U.S. PATENT DOCUMENTS

2016/0015012 A1* 1/2016 Quaggin ............ A01K 67/0278 800/3

* cited by examiner

*Primary Examiner* — Michael Burkhart
(74) *Attorney, Agent, or Firm* — Venable LLP; Keith G. Haddaway; Miguel A. Lopez (57) ABSTRACT

The present invention relates to a vector construct, and more specifically to a vector construct comprising human hypoxia inducible factor α gene. The present invention also relates to a transgenic animal or cell containing said vector construct which in the presence of an inducing agent expresses human hypoxia inducible factor α gene causing hair growth suppression. The present invention further relates to use of this animal model for determining the efficacy of methods for suppressing or inducing hair growth and discover further molecules which regulate hair growth.

6 Claims, 7 Drawing Sheets

VECTOR CONSTRUCT WITH HUMAN HYPOXIA INDUCIBLE FACTOR α GENE

CROSS-REFERENCE TO PRIOR APPLICATIONS

This application claims priority to U.S. Provisional Application No. 61/994,657 filed May 16, 2014, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on May 15, 2015, is named 127325-385622_SL.txt and is 19,050 bytes in size.

BACKGROUND OF THE INVENTION

Area of the Art

The present invention relates to a vector construct, and more specifically to a vector construct comprising human hypoxia inducible factor 2 α gene. The present invention also relates to a transgenic animal or cell containing said vector construct which in the presence of an inducing agent expresses human hypoxia inducible factor 2 α gene causing hair growth suppression. The present invention further relates to use of this animal model for determining the efficacy of potential agents for suppressing or inducing hair growth.

Description of the Background Art

Although hair naturally grows over most of the human body, excessive growth or growth in certain areas may be undesirable. Hair can be removed by shaving, chemical depilatories, waxing, sugaring, threading, electrolysis and laser. Only the latter two methods are considered "permanent". Many of the non-permanent methods are time consuming, the results are temporary, and the procedure must be repeated. The so-called permanent solutions are time consuming and costly. All of the procedures may be painful or uncomfortable.

There is no known inducible hair growth suppression gene in animal models on which potential agents for suppressing and inducing hair growth can be measured. Although transgenic animals are known, and one of the best known examples is the "Harvard Mouse" which is described in U.S. Pat. No. 4,736,866, there is no transgenic animal or cell capable of inducing hair growth suppression.

Thus there is a need for a vector construct with inducible hair growth suppression gene, as well as cells incorporating such a vector construct and a transgenic animal model incorporating such a vector construct.

SUMMARY OF THE INVENTION

The present invention relates to the construction of a vector with an inducible hair growth suppression gene, as well as cells incorporating such a vector construct and a transgenic animal model incorporating such a vector construct.

In some embodiments, the invention relates to the creation of a vector construct which in a transgenic mouse model produces hypoxia inducible factor α ("HIF2α") in the presence of an inducing agent resulting in suppression of hair growth. The degree of hair loss ranges from complete baldness to moderate hair loss as compared to normal mice.

Also, in some embodiments, the HIF2α incorporated into the vector and expressed in transgenic mice can be modified such that its function and/or expression can be controlled. Modifications can also prevent the degradation of HIF2α, while keeping it transcriptionally active. In some embodiments engineered changes to the gene/protein can work to prevent hydroxylation of HIF2α, allowing it to escape proteasome degradation, and remain transcriptionally active.

Furthermore, in some embodiments, transgenic organisms or cells expressing the constructed vector can be used to study hair growth or loss and compounds, agents or chemicals that influence hair growth or loss.

DESCRIPTION OF THE FIGURES

FIGS. 3a AND 3b show a single mouse from one of four founding lines overexpressing HIF2α in an embodiment of the present invention.

FIGS. 4a-4d show mice induced with doxycyline (DOX).

DETAILED DESCRIPTION OF THE INVENTION

The following description is provided to enable any person skilled in the art to make and use the invention and sets forth the best modes contemplated by the inventor of carrying out the invention. Various modifications, however, will remain readily apparent to those skilled in the art, since the general principles of the present invention have been defined herein specifically to provide an example and clarity.

Embodiments of the present invention relate to a mutated human hypoxia inducible factor α gene and a vector construct comprising mutated human hypoxia inducible factor α gene. Embodiments of the present invention also relate to a transgenic animal or cell containing said mutated human hypoxia inducible factor α gene or said vector construct which in the presence of an inducing agent expresses human hypoxia inducible factor α gene causing hair growth suppression. Embodiments of the present invention further relate to use of this animal or cell model for determining the efficacy of agents to suppress or induce hair growth.

Embodiments of the present invention relate to the creation of a vector construct which in a transgenic mouse model produces hypoxia inducible factor α ("HIF2α") in the presence of an inducing agent resulting in suppression of hair growth. The degree of hair loss when the vector construct is capable of being induced in vivo, ranges from complete baldness (homozygous) to moderate hair loss (heterozygous) compared to normal mice.

The following description details one method to obtain a vector construct as well as cells and a transgenic animal model, specifically a mouse model, with human HIF2α genes that are inducible and result in mice with phenotypes ranging from normal to bald appearance.

Figure 1:
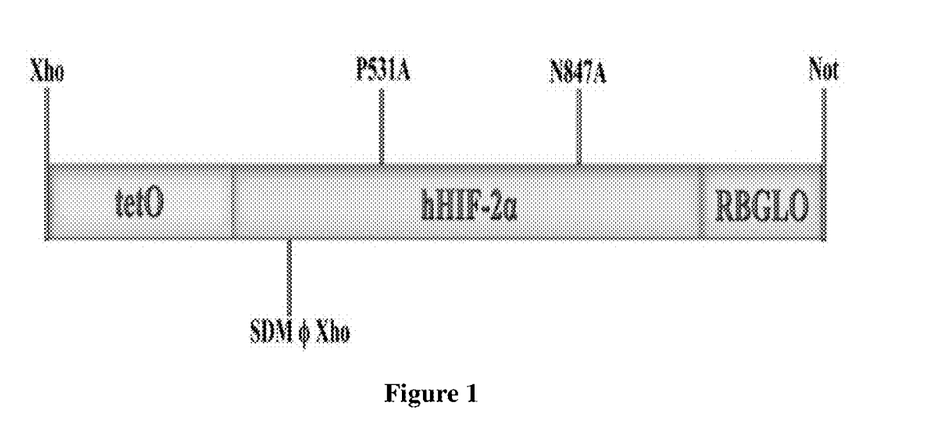
FIG. 1 shows a mutated human HIF2α of an embodiment of the present invention.

Using site-directed mutagenesis, both Proline531 and Asparagine847 of the human HIF2α were replaced with one Alanine each. Site directed mutagenesis was conducted using commercially available kits, for example, TAKARA PrimeSTAR MAX DNA polymerase for site-directed mutagenesis, and followed the manufacturer's instructions. Enzyme information can be found at http://www.clontech.com/takara/US/Products/PCR_Products/High_Fidelity_PCR/PrimeSTAR_Max_DNA_Polymerase. Replacing Proline531 and Asparagine847 of the human HIF2α with one Alanine each changes the function of HIF2α, namely it becomes very active so that the levels of the protein can be controlled and accordingly a mouse with such changes is unique. It also prevents the degradation of HIF2α, while keeping it transcriptionally active. More specifically, the alteration prevents hydroxylation of HIF2α at two critical regions which allows it to escape proteasome degradation, and remain transcriptionally active by immutably binding the transcriptional co-factors CBP/p300. FIG. 1 shows this mutated human HIF2α.

Figure 2:
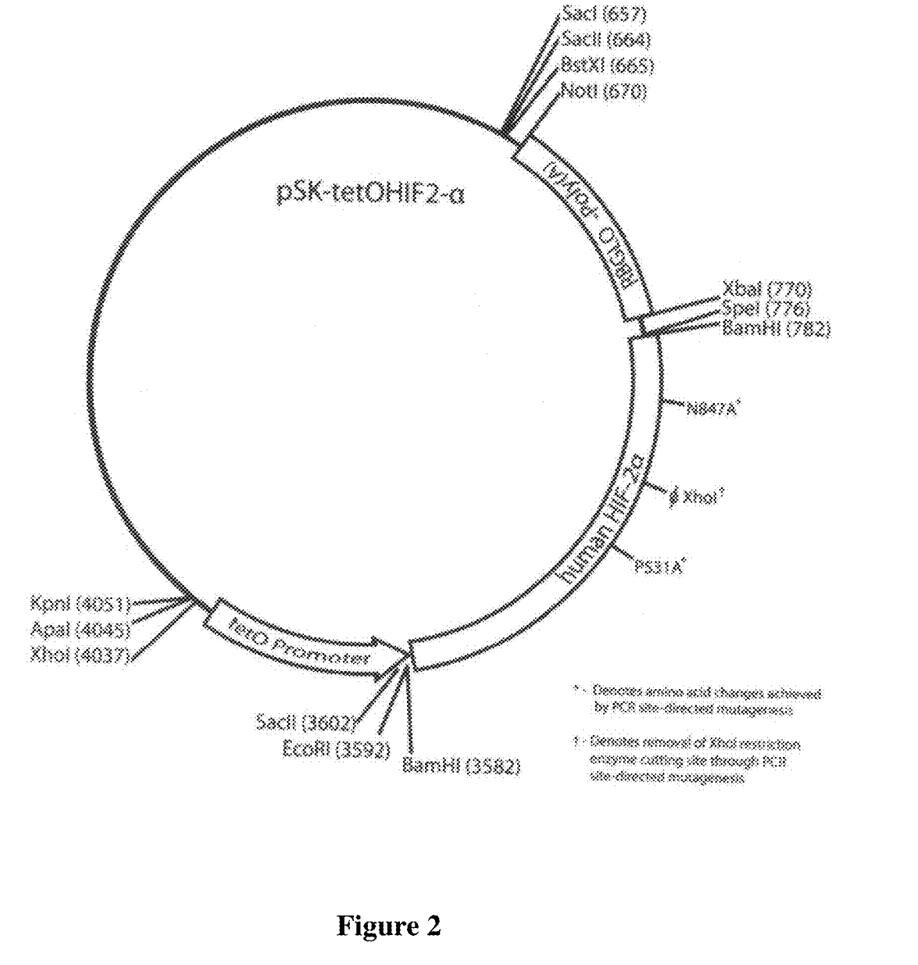
FIG. 2 is shows a tetO-HIF2α Vector Construct of an embodiment of the present invention.

A tetO-HIF2α Vector Construct of the present invention is shown in FIG. 2. Briefly, standard molecular cloning techniques apparent to anyone of ordinary skill in the art were employed to construct the plasmid. However, the design of the plasmid including the determination of where to insert the amino acid substitutions was the result of non-obvious design. A 2.8 kb BamHI fragment of the mutated HIF2α cDNA was inserted into the pSK-tetCRE vector and additionally a 0.97 kb NotI-XbaI fragment containing a rabbit β-globin polyadenylation signal was also introduced in the same location.

The BamHI fragment (containing Cre and the MT-I PolyA) was removed from pSK-tetCre (p176). The BamHI fragment (containing the mutated human HIF2-α) from pEF-HIF2 α BOS was excised and ligated into this region (about 2.8 kb). The NotI-XbaI fragment (containing the RBGLO polyA) was excised from PNxPRS-nephrin promoter (p130) and ligated in the corresponding location (about 1 kb).

The mutated HIF2α vector construct was introduced into the mouse genome of a one cell mouse embryo using standard technology described in, for example, Manipulating the Mouse Embryo: A Laboratory Manual. Nagy, A, Gertsenstein, M, Vintersten, K, Behringer, R. 2003. Cold Spring Harbor Press. New York. The pups were born transgenic with the inserted DNA incorporated into their genome which will be passed from generation to generation. Mice found to contain the inducible HIF2α construct are referred to as tetO-HIF2α mice.

To generate an inducible transgenic mouse, the tetO-HIF2α mice were bred to a mouse line that carries a ROSA26-rtTA transgene. The ROSA26-rtTA transgenic line was first described in Belteki G., Haigh J., Kabacs N., Haigh K., Sison K., Costantini F., Whitsett J., Quaggin S. E., Nagy A. Conditional and inducible transgene expression in mice through the combinatorial use of Cre mediated recombination and tetracycline induction. Nucleic Acids Res. 2005; 33:e51. Jackson Laboratories stock no. 005572. The use of PCR to identify the transgenic mice is described further below. Other mouse lines can be utilized, including hair-follicle specific drivers instead of ROSA. The coding sequence for reverse tetracycline transactivator (rtTA) was targeted into the ubiquitously expressed ROSA26 locus, which drives expression in all cells upon addition of the inducing agent, doxycycline. Thus the HIF2α will only be expressed in the presence of an inducer, which in this case is the antibiotic doxycycline.

The transgenic mice were induced using doxycycline (DOX) at P0 (day of birth).

The result in this particular experiment was five independent founding lines named #2, #20, #29, #34 and #36. Four of the resulting five founding lines, namely lines #2, #20, #29 and #36 displayed a similar mutant phenotype with baldness ranging from moderate to complete, and these four expressed the gene in the presence of the inducer, doxycycline. Three of these four mice, namely lines #2, #20 and #29 developed baldness only when the gene is switched on in the presence of doxycycline, and when the gene is switched off (doxycycline is removed) the mice grew back their hair within one week.

Figure 3A:
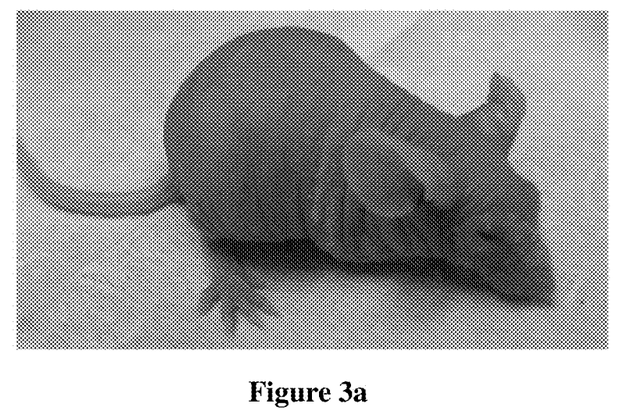
FIG. 3a is the mouse following induction of a transgene and FIG. 3b is the mouse within twenty four hours following removal of the inducing agent, namely stopping doxycycline.
Figure 3B:
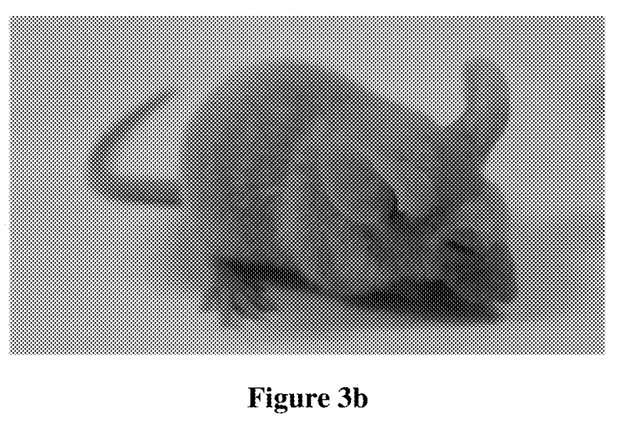

FIG. 3 is a single mouse from one of the four founding lines overexpressing HIF2α. Doxycycline induction of the transgene results in a completely bald mouse (FIG. 3a). Cessation of doxycycline (DOX) results in hair re-growth within 24 hours as seen in FIG. 3b.

Figure 4A:
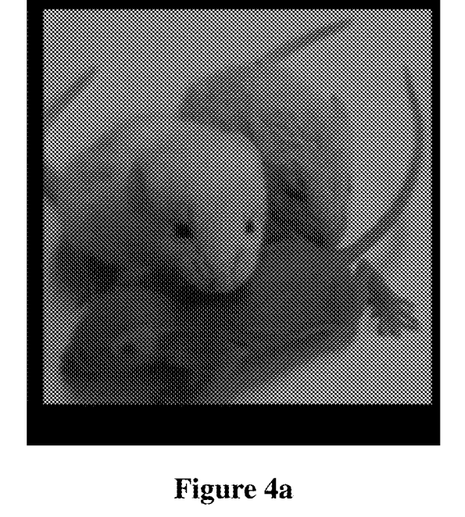
FIG. 4a shows, three littermate mice in an embodiment of the present invention after induction with doxycycline, namely (clockwise from upper left), a wild type mouse, heterozygous mouse and homozygous mouse.
Figure 4B:
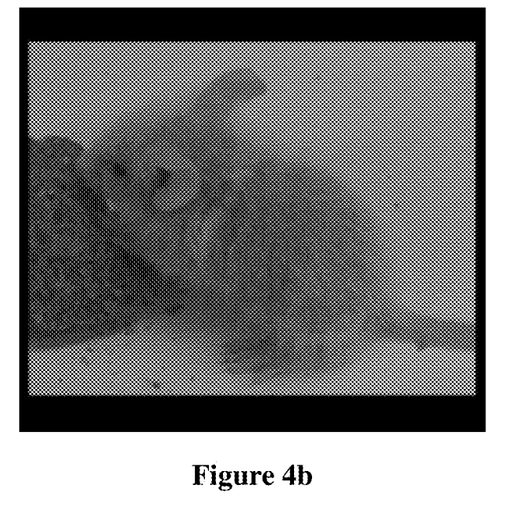
FIGS. 4b-d show induction of the same heterozygous mouse for three days of doxycycline (FIG. 4b), seven days of doxycycline (FIG. 4c) and twenty four hours after stopping induction (FIG. 4d).
Figure 4C:
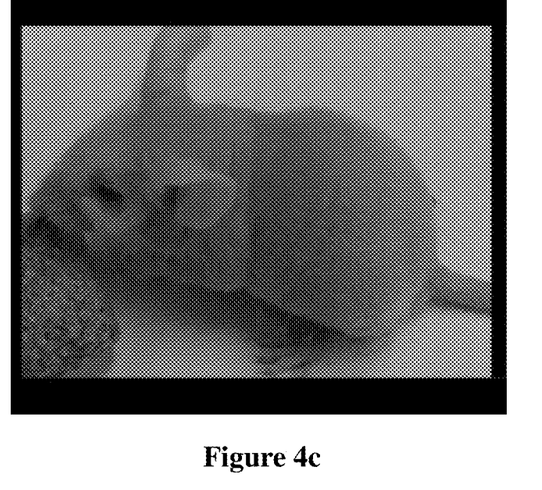
Figure 4D:
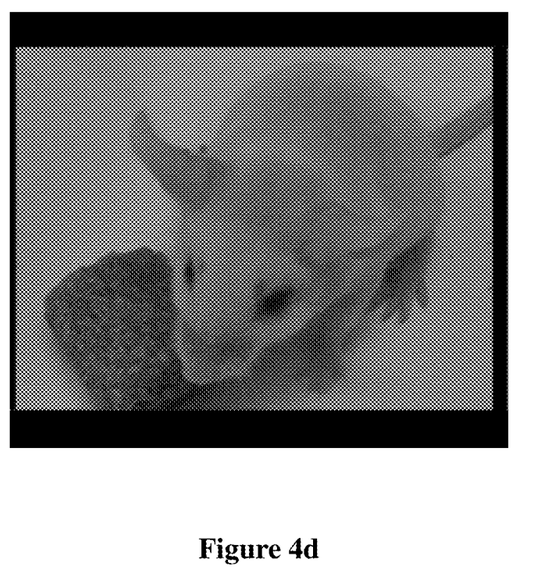

FIG. 4a shows three littermates being induced with doxycycline represent (clockwise from upper left), a wild type mouse (0 transgenes, line #20), heterozygous mouse (1 transgene, line #20) and homozygous mouse (2 transgenes, line #20). The correlation is that the higher the amount of HIF2α that is in the mouse, the greater the degree of baldness. FIG. 4b shows a mouse induced with DOX for three days which caused hair loss. FIG. 4c shows the same mouse after induction with DOX for seven days resulting in almost complete baldness. FIG. 4d shows the same mouse 24 hours after stopping induction.

Figure 5A:
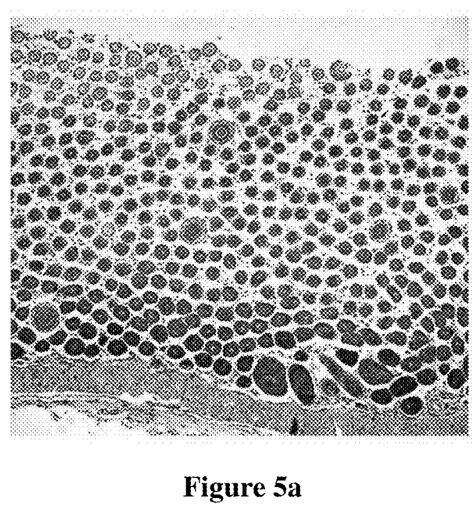
FIGS. 5a and 5b show skin samples from mice after induction with doxycycline, namely line #20, an embodiment of the present invention (FIG. 5b), and a control mouse (FIG. 5a).
Figure 5B:
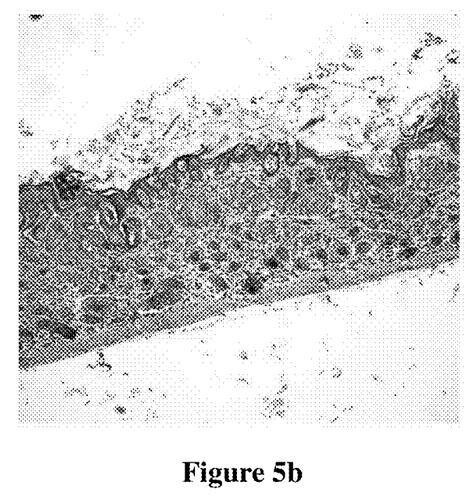

Line #20 when induced with DOX did not grow any hair. When DOX was removed, hair regrew. When induced with DOX again, line #20 mice began to lose their hair. Skin samples from mice in line #20 were collected and are shown in FIG. 5b and compared in FIG. 5a with skin cells from a control mouse. Histologic analysis of the hair follicles in these mice has been conducted and shows that the bald transgenic mice contain abnormal hair follicles. The mouse skin cells from line #20 show a lack of organized layers of active hair follicles in the transgenic mouse during induction of HIF2α. This demonstrates that HIF2α can affect hair growth and hair follicle maintenance.

The tetO-HIF2α Vector Construct shown in FIG. 2 produces a stabilized form of HIF2α as proven by real-time PCR to measure the levels of HIF2α mRNA. Progeny of the tetO-HIF2α and ROSA26-rtTA mice were screened for both transgenes using PCR. This was accomplished by isolating genomic DNA from mouse tails and using PCR to identify double transgenic mice using the primers ROSArtTA (SEQ ID NO. 4 and SEQ ID NO. 5). and HIF2α (SEQ ID NO. 6 and SEQ ID NO. 7). Presence of the transgene was confirmed by 453bp, 430bp bands respectively.

Total RNA was extracted from mouse liver samples and reverse transcribed into cDNA using M-MLV reverse transcriptase and random hexamer primers. cDNA samples were amplified and analyzed in duplicates. Primers were designed and validated to determine efficiency and these primers for HIF2α (SEQ ID NO. 8 and SEQ ID NO. 9) and GAPDH (SEQ ID NO. 10 and SEQ ID NO. 11) The GAPDH house-keeping gene was used as an internal control. SEQ ID NO. 8 and SEQ ID NO. 9 generated a fragment of 156 by in size, while SEQ ID NO. 10 and SEQ ID NO. 11 generated a fragment of 430 by in size.

Figure 6:
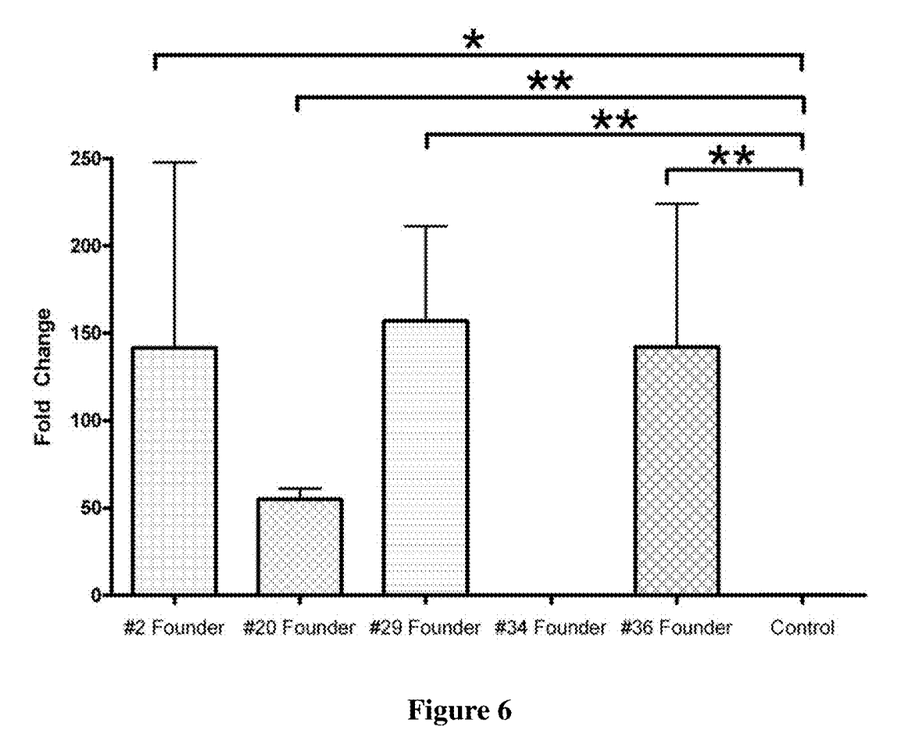
FIG. 6 shows HIF2α mRNA levels of four of the five founding lines (lines #2, #20, #29 and #36) in an embodiment of the present invention, compared to control mice.

Four of the five founding lines (lines #2, #20, #29 and #36) showed a robust increase in HIF2α mRNA levels when compared to control mice as shown in FIG. 6. The average fold-changes were 141.6-fold, 54.9-fold, 157.1-fold and 142.1-fold in the lines #2, #20, #29 and #36 founding lines, respectively, when compared to control mice ($P<0.02$, $P<0.005$, $P<0.003$, and $P<0.001$ respectively). The #34 founding line did not show any appreciable increase in HIF2α mRNA expression (0.1-fold increase) when compared to control littermates (n=3), which correlated with the fact that no visible phenotype was apparent in the #34 mice, that is, no baldness.

Despite different insertion sites, all four lines of mice exhibit the same phenotype demonstrating that it is due to the HIF2α transgene and not due to disruption of another gene.

The DNA sequence for this mutated human HIF2α construct is set out in SEQ ID NO: 1. The DNA sequence for the cDNA of this mutated human HIF2α construct is set out in SEQ ID NO: 2. The amino acid sequence for this mutated human HIF2α construct is set out in SEQ ID NO: 3.

This system may be used to understand baldness, discover molecules regulating hair growth, to understand the HIF2α gene, and putative therapeutic targets as well as hair removal therapies since the Vector Construct when induced by the presence of doxycycline causes hair loss. This inducible construct is useful to determine molecular pathways responsible for hair growth and baldness.

The HIF2α regulated pathway is a therapeutic target to treat baldness. A molecule that can degrade HIF2α or one of its critical targets will have promise in reversing baldness. Such a molecule may be tested on the heterozygous or homozygous mice in the presence of DOX to determine if it can reverse the hair loss and allow hair to regrow.

Alternatively, delivery of HIF2α to hair follicles in areas of the body on which hair is unwanted will aid in eliminating hair growth.

From the above detailed description of the invention, the operation and construction of same should be apparent. While there are herein shown and described example embodiments of the invention, it is nevertheless understood that various changes may be made with respect thereto without departing from the principle and scope of the invention as measured by the following claims.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

```
Sequence Listing

SEQ ID NO. 1
CCTATCAGTGATAGAGAAAAGTGAAAGTCGAGTTTACCACTCCCTATCAGTGATAGAGAAAAGTGAAA
GTCGAGTTTACCACTCCCTATCAGTGATAGAGAAAAGTGAAAGTCGAGTTTACCACTCCCTATCAGTG
ATAGAGAAAAGTGAAAGTCGAGTTTACCACTCCCTATCAGTGATAGAGAAAAGTGAAAGTCGAGTTTA
CCACTCCCTATCAGTGATAGAGAAAAGTGAAAGTCGAGTTTACCACTCCCTATCAGTGATAGAGAAAA
GTGAAAGTCGAGCTCGGTACCCGGGTCGAGGTAGGCGTGTACGGTGGGAGGCCTATATAAGCAGAGCT
CGTTTAGTGAACCGTCAGATCGCCTGGAGACGCCATCCACGCTGTTTTGACCTCCATAGAAGACACCG
GGACCGATCCAGCCTCCGCGGCCCCGAATTCGAGCTCGGTACCCGGGGATCCCTGCAGGCCTCGAC*C
CTGACTGCGCGGGCGCTCGGGACCTGCGCGCACCTCGGACCTTCACCACCCGCCCGGGCCGCGGGGA
GCGGACGAGGGCCACAGCCCCCCACCCGCCAGGGAGCCCAGGTGCTCGGCGTCTGAACGTCTCAAAGG
GCCACAGCGACAATGACAGCTGACAAGGAGAAGAAAAGGAGTAGCTCGGAGAGGAGGAAGGAGAAGTC
CCGGGATGCTGCGCGGTGCCGGCGGAGCAAGGAGACGGAGGTGTTCTATGAGCTGGCCCATGAGCTGC
CTCTGCCCCACAGTGTGAGCTCCCATCTGGACAAGGCCTCCATCATGCGACTGGCAATCAGCTTCCTG
CGAACACACAAGCTCCTCTCCTCAGTTTGCTCTGAAAACGAGTCCGAAGCCGAAGCTGACCAGCAGAT
GGACAACTTGTACCTGAAAGCCTTGGAGGGTTTCATTGCCGTGGTGACCCAAGATGGCGACATGATCT
TTCTGTCAGAAAACATCAGCAAGTTCATGGGACTTACACAGGTGGAGCTAACAGGACATAGTATCTTT
GACTTCACTCATCCCTGCGACCATGAGGAGATTCGTGAGAACCTGAGTCTCAAAAATGGCTCTGGTTT
TGGGAAAAAAAGCAAAGACATGTCCACAGAGCGGGACTTCTTCATGAGGATGAAGTGCACGGTCACCA
ACAGAGGCCGTACTGTCAACCTCAAGTCAGCCACCTGGAAGGTCTTGCACTGCACGGGCCAGGTGAAA
GTCTACAACAACTGCCCTCCTCACAATAGTCTGTGTGGCTACAAGGAGCCCCTGCTGTCCTGCCTCAT
CATCATGTGTGAACCAATCCAGCACCCATCCCACATGGACATCCCCCTGGATAGCAAGACCTTCCTGA
GCCGCCACAGCATGGACATGAAGTTCACCTACTGTGATGACAGAATCACAGAACTGATTGGTTACCAC
CCTGAGGAGCTGCTTGGCCGCTCAGCCTATGAATTCTACCATGCGCTAGACTCCGAGAACATGACCAA
GAGTCACCAGAACTTGTGCACCAAGGGTCAGGTAGTAAGTGGCCAGTACCGGATGCTCGCAAAGCATG
GGGGCTACGTGTGGCTGGAGACCCAGGGGACGGTCATCTACAACCCTCGCAACCTGCAGCCCCAGTGC
ATCATGTGTGTCAACTACGTCCTGAGTGAGATTGAGAAGAATGACGTGGTGTTCTCCATGGACCAGAC
TGAATCCCTGTTCAAGCCCCACCTGATGGCCATGAACAGCATCTTTGATAGCAGTGGCAAGGGGGCTG
TGTCTGAGAAGAGTAACTTCCTATTCACCAAGCTAAAGGAGGAGCCCGAGGAGCTGGCCCAGCTGGCT
CCCACCCCAGGAGACGCCATCATCTCTCTGGATTTCGGGAATCAGAACTTCGAGGAGTCCTCAGCCTA
TGGCAAGGCCATCCTGCCCCCGAGCCAGCCATGGGCCACGGAGTTGAGGAGCCACAGCACCCAGAGCG
AGGCTGGGAGCCTGCCTGCCTTCACCGTGCCCCAGGCAGCTGCCCCGGGCAGCACCACCCCCAGTGCC
ACCAGCAGCAGCAGCAGCTGCTCCACGCCCAATAGCCCTGAAGACTATTACACATCTTTGGATAACGA
CCTGAAGATTGAAGTGATTGAGAAGCTCTTCGCCATGGACACAGAGGCCAAGGACCAATGCAGTACCC
AGACGGATTTCAATGAGCTGGACTTGGAGACGCTAGCAGCCTATATCCCCATGGACGGGGAAGACTTC
CAGCTAAGCCCCATCTGCCCCGAGGAGCGGCTCTTGGCGGAGAACCCACAGTCCACCCCCCAGCACTG
CTTCAGTGCCATGACAAACATCTTCCAGCCACTGGCCCCTGTAGCCCCGCACAGTCCCTTCCTCCTGG
ACAAGTTTCAGCAGCAGCTGGAGAGCAAGAAGACAGAGCCCGAGCACCGGCCCATGTCCTCCATCTTC
TTTGATGCCGGAAGCAAAGCATCCCTGCCACCGTGCTGTGGCCAGGCCAGCACCCCTCTCTCTTCCAT
GGGGGGCAGATCCAATACCCAGTGGCCCCAGATCCACCATTACATTTTGGGCCCACAAAGTGGGCCG
TCGGGGATCAGCGCACAGAGTTCTTGGGAGCAGCGCCGTTGGGGCCCCCTGTCTCTCCACCCCATGTC
```

```
TCCACCTTCAAGACAAGGTCTGCAAAGGGTTTTGGGGCACGAGGCCCAGACGTGCTGAGTCCGGCCAT
GGTAGCCCTCTCCAACAAGCTGAAGCTGAAGCGACAGCTGGAGTATGAAGAGCAAGCCTTCCAGGACC
TGAGCGGGGGGGACCCACCTGGTGGCAGCACCTCACATTTGATGTGGAAACGGATGAAGAACCTCAGG
GGTGGGAGCTGCCCTTTGATGCCGGACAAGCCACTGAGCGCAAATGTACCCAATGATAAGTTCACCCA
AAACCCCATGAGGGGCCTGGGCCATCCCCTGAGACATCTGCCGCTGCCACAGCCTCCATCTGCCATCA
GTCCCGGGGAGAACAGCAAGAGCAGGTTCCCCCCACAGTGCTACGCCACCCAGTACCAGGACTACAGC
CTGTCGTCAGCCCACAAGGTGTCAGGCATGGCAAGCCGGCTGCTCGGGCCTCATTTGAGTCCTACCT
GCTGCCCGAACTGACCAGATATGACTGTGAGGTGGCGGTACCCGTGCTGGGAAGCTCCACGCTCCTGC
AAGGAGGGGACCTCCTCAGAGCCCTGGACCAGGCCACCTGACTGGACCAGGCCACCTGACGGATCCAC
TAGTTCTAGAGCTGAGAACTTCAGGGTGAGTTTGGGGACCCTTGATTGTTCTTTCTTTTTCGCTATTG
TAAAATTCATGTTATATGGAGGGGGCAAAGTTTTCAGGGTGTTGTTTAGAATGGGAAGATGTCCCTTG
TATCACCATGGACCCTCATGATAATTTTGTTTCTTTCACTTTCTACTCTGTTGACAACCATTGTCTCC
TCTTATTTTCTTTTCATTTTCTGTAACTTTTTCGTTAAACTTTAGCTTGCATTTGTAACGAATTTTTA
AATTCACTTTTGTTTATTTGTCAGATTGTAAGTACTTTCTCTAATCACTTTTTTTTCAAGGCAATCAG
GGTATATTATATTGTACTTCAGCACAGTTTTAGAGAACAATTGTTATAATTAAATGATAAGGTAGAAT
ATTTCTGCATATAAATTCTGGCTGGCGTGGAAATATTCTTATTGGTAGAAACAACTACACCCTGGTCA
TCATCCTGCCTTTCTCTTTATGGTTACAATGATATACACTGTTTGAGATGAGGATAAAATACTCTGAG
TCCAAACCGGGCCCCTCTGCTAACCATGTTCATGCCTTCTTCTCTTTCCTACAGCTCCTGGGCAACGT
GCTGGTTGTTGTGCTGTCTCATCATTTTGGCAAAGAATTCACTCCTCAGGTGCAGGCTGCCTATCAGA
AGGTGGTGGCTGGTGTGGCCAATGCCCTGGCTCACAAATACCACTGAGATCTTTTCCCTCTGCCAAA
AATTATGGGGACATCATGAAGCCCCTTGAGCATCTGACTTCTGGCTAATAAAGGAAATTTATTTTCAT
TGCAATAGTGTGTTGGAATTTTTTGTGTCTCTCACTCGGAAGGACATATGGGAGGGCAAATCATTTAA
AACATCAGAATGAGTATTTGGTTTAGAGTTTGGCACATATGCCCA

SEQ ID NO. 2:
CCTGACTGCGCGGGGCGCTCGGGACCTGCGCGCACCTCGGACCTTCACCACCCGCCCGGGCCGCGGGG
AGCGGACGAGGGCCACAGCCCCCCACCCGCCAGGGAGCCCAGGTGCTCGGCGTCTGAACGTCTCAAAG
GGCCACAGCGACAATGACAGCTGACAAGGAGAAGAAAAGGAGTAGCTCGGAGGAGGAAGGAGAAGT
CCCGGGATGCTGCGCGGTGCCGGCGGAGCAAGGAGACGGAGGTGTTCTATGAGCTGGCCCATGAGCTG
CCTCTGCCCCACAGTGTGAGCTCCCATCTGGACAAGGCCTCCATCATGCGACTGGCAATCAGCTTCCT
GCGAACACACAAGCTCCTCTCCTCAGTTTGCTCTGAAAACGAGTCCGAAGCCGAAGCTGACCAGCAGA
TGGACAACTTGTACCTGAAAGCCTTGGAGGGTTTCATTGCCGTGGTGACCCAAGATGGCGACATGATC
TTTCTGTCAGAAAACATCAGCAAGTTCATGGGACTTACACAGGTGGAGCTAACAGGACATAGTATCTT
TGACTTCACTCATCCCTGCGACCATGAGGAGATTCGTGAGAACCTGAGTCTCAAAAATGGCTCTGGTT
TTGGGAAAAAAAGCAAAGACATGTCCACAGAGCGGGACTTCTTCATGAGGATGAAGTGCACGGTCACC
AACAGAGGCCGTACTGTCAACCTCAAGTCAGCCACCTGGAAGGTCTTGCACTGCACGGGCCAGGTGAA
AGTCTACAACAACTGCCCTCCTCACAATAGTCTGTGTGGCTACAAGGAGCCCCTGCTGTCCTGCCTCA
TCATCATGTGTGAACCAATCCAGCACCCATCCCACATGGACATCCCCCTGGATAGCAAGACCTTCCTG
AGCCGCCACAGCATGGACATGAAGTTCACCTACTGTGATGACAGAATCACAGAACTGATTGGTTACCA
CCCTGAGGAGCTGCTTGGCCGCTCAGCCTATGAATTCTACCATGCGCTAGACTCCGAGAACATGACCA
AGAGTCACCAGAACTTGTGCACCAAGGGTCAGGTAGTAAGTGGCCAGTACCGGATGCTCGCAAAGCAT
GGGGGCTACGTGTGGCTGGAGACCCAGGGGACGGTCATCTACAACCCTCGCAACCTGCAGCCCCAGTG
CATCATGTGTGTCAACTACGTCCTGAGTGAGATTGAGAAGAATGACGTGGTGTTCTCCATGGACCAGA
CTGAATCCCTGTTCAAGCCCCACCTGATGGCCATGAACAGCATCTTTGATAGCAGTGGCAAGGGGGCT
GTGTCTGAGAAGAGTAACTTCCTATTCACCAAGCTAAAGGAGGAGCCTGAAGACTATTACACATCTTTGGATAACG
TCCCCACCCCAGGAGACGCCATCATCTCTCTGGATTTCGGGAATCAGAACTTCGAGGAGTCCTCAGCCT
ATGGCAAGGCCATCCTGCCCCCGAGCCAGCCATGGGCCACGGAGTTGAGGAGCCACAGCACCCAGAGC
GAGGCTGGGAGCCTGCCTGCCTTCACCGTGCCCCAGGCAGCTGCCCCGGGCAGCACCACCCCCAGTGC
CACCAGCAGCAGCAGCAGCTGCTCCACGCCCAATAGCCCTGAAGACTATTACACATCTTTGGATAACG
ACCTGAAGATTGAAGTGATTGAGAAGCTCTTCGCCATGGACACAGAGGCCAAGGACCAATGCAGTACC
CAGACGGATTTCAATGAGCTGGACTTGGAGACGCTAGCAGCCTATATCCCCATGGACGGGGAAGACTT
CCAGCTAAGCCCCATCTGCCCCGAGGAGCGGCTCTTGGCGGAGAACCCACAGTCCACCCCCCAGCACT
GCTTCAGTGCCATGACAAACATCTTCCAGCCACTGGCCCCTGTAGCCCCGCACAGTCCCTTCCTCCTG
GACAAGTTTCAGCAGCAGCTGGAGAGCAAGAAGACAGAGCCCGAGCACCGGCCCATGTCCTCCATCTT
CTTTGATGCCGGAAGCAAAGCATCCCTGCCACCGTGCTGTGGCCAGGCCAGCACCCCTCTCTCTTCCA
TGGGGGGCAGATCCAATACCCAGTGGCCCCAGATCCACCATTACATTTTGGGCCCACAAAGTGGGCC
GTCGGGGATCAGCGCACAGAGTTCTTGGGAGCAGCGCCGTTGGGGCCCCCTGTCTCTCCACCCCATGT
CTCCACCTTCAAGACAAGGTCTGCAAAGGGTTTTGGGGCACGAGGCCCCAGACGTGCTGAGTCCGGCA
TGGTAGCCCTCTCCAACAAGCTGAAGCTGAAGCGACAGCTGGAGTATGAAGAGCAAGCCTTCCAGGAC
CTGAGCGGGGGGACCCACCTGGTGGCAGCACCTCACATTTGATGTGGAAACGGATGAAGAACCTCAG
GGGTGGGAGCTGCCCTTTGATGCCGGACAAGCCACTGAGCGCAAATGTACCCAATGATAAGTTCACCC
AAAACCCCATGAGGGGCCTGGGCCATCCCCTGAGACATCTGCCGCTGCCACAGCCTCCATCTGCCATC
AGTCCCGGGGAGAACAGCAAGAGCAGGTTCCCCCCACAGTGCTACGCCACCCAGTACCAGGACTACAG
CCTGTCGTCAGCCCACAAGGTGTCAGGCATGGCAAGCCGGCTGCTCGGGCCTCATTTGAGTCCTACC
TGCTGCCCGAACTGACCAGATATGACTGTGAGGTGGCGGTACCCGTGCTGGGAAGCTCCACGCTCCTG
CAAGGAGGGGACCTCCTCAGAGCCCTGGACCAGGCCACCTGA

SEQ ID NO. 3:
MTADKEKKRSSSERRKEKSRDAARCRRSKETEVFYELAHELPLPHSVSSHLDKASIMRLAISFLRTHK
LLSSVCSENESEAEADQQMDNLYLKALEGFIAVVTQDGDMIFLSENISKFMGLTQVELTGHSIFDFTH
PCDHEEIRENLSLKNGSGFGKKSKDMSTERDFFMRMKCTVTNRGRTVNLKSATWKVLHCTGQVKVYNN
CPPHNSLCGYKEPLLSCLIIMCEPIQHPSHMDIPLDSKTFLSRHSMDMKFTYCDDRITELIGYHPEEL
LGRSAYEFYHALDSENMTKSHQNLCTKGQVVSGQYRMLAKHGGYVWLETQGTVIYNPRNLQPQCIMCV
NYVLSEIEKNDVVFSMDQTESLFKPHLMAMNSIFDSSGKGAVSEKSNFLFTKLKEEPEELAQLAPTPG
DAIISLDFGNQNFEESSAYGKAILPPSQPWATELRSHSTQSEAGSLPAFTVPQAAAPGSTTPSATSSS
SSCSTPNSPEDYYTSLDNDLKIEVIEKLFAMDTEAKDQCSTQTDFNELDLETLAAYIPMDGEDFQLSP
ICPEERLLAENPQSTPQHCFSAMTNIFQPLAPVAPHSPFLLDKFQQQLESKKTEPEHRPMSSIFFDAG
```

SKASLPPCCGQASTPLSSMGGRSNTQWPPDPPLHFGPTKWAVGDQRTEFLGAAPLGPPVSPPHVSTFK
TRSAKGFGARGPDVLSPAMALSNKLKLKRQLEYEEQAFQDLSGGDPPGGSTSHLMWKRMKNLRGGSCP
LMPDKPLSANVPNDKFTQNPMRGLGHPLRHLPLPQPPSAISPGENSKSRFPPQCYATQYQDYSLSSAH
KVSGMASRLLGPSFESYLLPELTRYDCEVAVPVLGSSTLLQGGDLLRALDQAT

SEQ ID NO. 4
GAGTTCTCTGCTGCCTCCTG

SEQ ID NO. 5
AGCTCTAATGCGCTGTTAAT

SEQ ID NO. 6
TCCACCCCATGTCTCCACCT

SEQ ID NO. 7
GCCATGCCTGACACCTTGTG

SEQ ID NO. 8
TTGATGTGGAAACGGATGAA

SEQ ID NO. 9
GGAACCTGCTCTTGCTGTTC

SEQ ID NO. 10
CACCACAGTCCATGCCATCACT

SEQ ID NO. 11
TCCACCACCCTGTTGCTGTAG

I claim:

1. A cDNA molecule of a vector construct coding for a human hypoxia inducible factor α polypeptide comprising a polynucleotide having the nucleotide sequence of SEQ ID NO:2.

2. A genetically modified non-human mammal or genetically modified non-human mammal cell transformed with a vector construct coding for a human hypoxia inducible factor α polypeptide comprising a polynucleotide having the nucleotide sequence of SEQ ID NO:1 wherein transcription of said human hypoxia inducible factor α polypeptide is under the control of a reverse tetracycline transactivator.

3. The mammal or cell of claim 2 wherein said transactivator is inducible in the presence of doxycycline.

4. A method of testing a material suspected of altering hair growth in a mammal comprising:
   (a) inducing expression of the human hypoxia factor α polypeptide in the mammal of claim 2;
   (b) administering a material or compound suspected of altering hair growth to the mammal expressing the human hypoxia factor α polypeptide; and
   (c) comparing hair growth or loss in the mammal expressing the human hypoxia factor α polypeptide and administered the material or compound to a control mammal not administered the material or compound.

5. A method of testing a material suspected of altering hair growth in a mammal comprising:
   (a) inducing expression of the human hypoxia factor α polypeptide in the mammal of claim 2 for a period of time sufficient to see aberrant hair expression;
   (b) reducing expression of the human hypoxia factor α polypeptide in the mammal;
   (c) administering a material or compound suspected of altering hair growth to the mammal with reduced expression of the human hypoxia factor α polypeptide; and
   (d) comparing hair growth or loss in the mammal with reduced expression of the human hypoxia factor α polypeptide and administered the material or compound to a control mammal not administered the material or compound.

6. A method of producing a transgenic cell culture, comprising;
   (a) introducing the vector construct coding for a human hypoxia inducible factor α polypeptide comprising a polynucleotide having the nucleotide sequence of SEQ ID NO:1 into a one cell mouse embryo;
   (b) allowing said embryo to develop into an adult mouse; and
   (c) culturing somatic cells of said mouse.

* * * * *

SEQUENCE LISTING

<160> NUMBER OF SEQ ID NOS: 11

<210> SEQ ID NO 1
<211> LENGTH: 4192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cctatcagtg atagagaaaa gtgaaagtcg agtttaccac tccctatcag tgatagagaa      60
aagtgaaagt cgagtttacc actccctatc agtgatagag aaaagtgaaa gtcgagttta     120
ccactcccta tcagtgatag agaaaagtga agtcgagtt taccactccc tatcagtgat      180
agagaaaagt gaaagtcgag tttaccactc cctatcagtg atagagaaaa gtgaaagtcg     240
agtttaccac tccctatcag tgatagagaa aagtgaaagt cgagctcggt acccgggtcg     300
aggtaggcgt gtacggtggg aggcctatat aagcagagct cgtttagtga accgtcagat     360
cgcctggaga cgccatccac gctgttttga cctccataga agacaccggg accgatccag     420
cctccgcggc cccgaattcg agctcggtac ccggggatcc ctgcaggcct cgaccctgac     480
tgcgcggggc gctcgggacc tgcgcgcacc tcggaccttc accacccgcc cgggccgcgg     540
ggagcggacg agggccacag ccccccaccc gccagggagc ccaggtgctc ggcgtctgaa     600
cgtctcaaag ggccacagcg acaatgacag ctgacaagga gaagaaagg agtagctcgg      660 agaggaggaa ggagaagtcc cgggatgctg cgcggtgccg gcggagcaag gagacggagg     720
tgttctatga gctggcccat gagctgcctc tgccccacag tgtgagctcc catctggaca     780
aggcctccat catgcgactg gcaatcagct cctgcgaac acacaagctc ctctcctcag      840
tttgctctga aaacgagtcc gaagccgaag ctgaccagca gatggacaac ttgtacctga     900

```
aagccttgga gggtttcatt gccgtggtga cccaagatgg cgacatgatc tttctgtcag    960
aaaacatcag caagttcatg ggacttacac aggtggagct aacaggacat agtatctttg   1020
acttcactca tccctgcgac catgaggaga ttcgtgagaa cctgagtctc aaaaatggct   1080
ctggttttgg gaaaaaaagc aaagacatgt ccacagagcg ggacttcttc atgaggatga   1140
agtgcacggt caccaacaga ggccgtactg tcaacctcaa gtcagccacc tggaaggtct   1200
tgcactgcac gggccaggtg aaagtctaca caactgccc tcctcacaat agtctgtgtg    1260
gctacaagga gcccctgctg tcctgcctca tcatcatgtg tgaaccaatc cagcacccat   1320
cccacatgga catcccctg gatagcaaga ccttcctgag ccgccacagc atggacatga    1380
agttcaccta ctgtgatgac agaatcacag aactgattgg ttaccaccct gaggagctgc   1440
ttggccgctc agcctatgaa ttctaccatg cgctagactc cgagaacatg accaagagtc   1500
accagaactt gtgcaccaag ggtcaggtag taagtggcca gtaccggatg ctcgcaaagc   1560 atggggcta cgtgtggctg agacccagg ggacggtcat ctacaaccct cgcaacctgc     1620
agccccagtg catcatgtgt gtcaactacg tcctgagtga gattgagaag aatgacgtgg   1680
tgttctccat ggaccagact gaatccctgt tcaagcccca cctgatggcc atgaacagca   1740
tctttgatag cagtggcaag ggggctgtgt ctgagaagga taacttccta ttccaccaagc  1800 taaaggagga gcccgaggag ctggcccagc tggctcccac cccaggagac gccatcatct   1860
ctctggattt cgggaatcag aacttcgagg agtcctcagc ctatggcaag gccatcctgc   1920
ccccgagcca gccatgggcc acggagttga ggagccacag cacccagagc gaggctggga   1980
gcctgcctgc cttcaccgtg ccccaggcag ctgccccggg cagcaccacc cccagtgcca   2040
ccagcagcag cagcagctgc tccacgccca atagccctga agactattac acatctttgg   2100
ataacgacct gaagattgaa gtgattgaga agctcttcgc catggacaca gaggccaagg   2160
accaatgcag tacccagacg gatttcaatg agctggactt ggagacgcta gcagcctata   2220
tccccatgga cggggaagac ttccagctaa gcccatctg ccccgaggag cggctcttgg    2280
cggagaaccc acagtccacc ccccagcact gcttcagtgc catgacaaac atcttccagc   2340
cactggcccc tgtagccccg cacagtccct tcctcctgga caagtttcag cagcagctgg   2400
agagcaagaa gacagagccc gagcaccggc ccatgtcctc catcttcttt gatgccggaa   2460
gcaaagcatc cctgccaccg tgctgtggcc aggccagcac ccctctctct tccatggggg   2520
gcagatccaa tacccagtgg ccccagatc caccattaca ttttgggccc acaaagtggg    2580
ccgtcgggga tcagcgcaca gagttcttgg gagcagcgcc gttggggccc cctgtctctc   2640 cacccccatgt ctccaccttc aagacaaggt ctgcaaaggg ttttgggca cgaggcccag   2700 acgtgctgag tccggccatg gtagccctct ccaacaagct gaagctgaag cgacagctgg   2760
agtatgaaga gcaagccttc caggacctga gcgggggga cccacctggt ggcagcacct   2820
cacatttgat gtggaaacgg atgaagaacc tcagggtgg gagctgccct ttgatgccgg    2880
acaagccact gagcgcaaat gtacccaatg ataagttcac ccaaaacccc atgagggcc    2940 tgggccatcc cctgagacat ctgccgctgc cacagcctcc atctgccatc agtcccgggg   3000
agaacagcaa gagcaggttc cccccacagt gctacgccac ccagtaccag gactacagcc   3060
tgtcgtcagc ccacaaggtg tcaggcatgg caagccggct gctcgggccc tcatttgagt   3120
cctacctgct gcccgaactg accagatatg actgtgaggt ggcggtaccc gtgctgggaa   3180
gctccacgct cctgcaagga ggggaccctcc tcagagccct ggaccaggcc acctgactgg   3240
accaggccac ctgacggatc cactagttct agagctgaga acttcagggt gagtttgggg   3300
```

```
accccttgatt gttctttctt tttcgctatt gtaaaattca tgttatatgg aggggggcaaa    3360 gttttcaggg tgttgtttag aatgggaaga tgtcccttgt atcaccatgg accctcatga    3420
taattttgtt tctttcactt tctactctgt tgacaaccat tgtctcctct tattttcttt    3480
tcattttctg taacttttc gttaaacttt agcttgcatt tgtaacgaat ttttaaattc    3540
acttttgttt atttgtcaga ttgtaagtac tttctctaat cactttttttt tcaaggcaat    3600 cagggtatat tatattgtac ttcagcacag ttttagagaa caattgttat aattaaatga    3660
taaggtagaa tatttctgca tataaattct ggctggcgtg gaaatattct tattggtaga    3720
aacaactaca ccctggtcat catcctgcct ttctctttat ggttacaatg atatacactg    3780
tttgagatga ggataaaata ctctgagtcc aaaccgggcc cctctgctaa ccatgttcat    3840
gccttcttct ctttcctaca gctcctgggc aacgtgctgg ttgttgtgct gtctcatcat    3900
tttggcaaag aattcactcc tcaggtgcag gctgcctatc agaaggtggt ggctggtgtg    3960
gccaatgccc tggctcacaa ataccactga gatcttttc cctctgccaa aaattatggg    4020
gacatcatga agccccttga gcatctgact tctggctaat aaaggaaatt tattttcatt    4080
gcaatagtgt gttggaattt tttgtgtctc tcactcggaa ggacatatgg gagggcaaat    4140
catttaaaac atcagaatga gtatttggtt tagagtttgg cacatatgcc ca           4192
```

<210> SEQ ID NO 2
<211> LENGTH: 2762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
cctgactgcg cggggcgctc gggacctgcg cgcacctcgg accttcacca cccgcccggg      60
ccgcggggag cggacgaggg ccacagcccc ccacccgcca gggagcccag gtgctcggcg     120
tctgaacgtc tcaaagggcc acagcgacaa tgacagctga caaggagaag aaaaggagta     180
gctcggagag gaggaaggag aagtcccggg atgctgcgcg gtgccggcgg agcaaggaga     240
cggaggtgtt ctatgagctg gcccatgagc tgcctctgcc ccacagtgtg agctcccatc     300
tggacaaggc ctccatcatg cgactggcaa tcagcttcct gcgaacacac aagctccctct     360 cctcagtttg ctctgaaaac gagtccgaag ccgaagctga ccagcagatg gacaacttgt     420
acctgaaagc cttggagggt ttcattgccg tggtgaccca agatggcgac atgatctttc     480
tgtcagaaaa catcagcaag ttcatgggac ttacacaggt ggagctaaca ggacatagta     540
tctttgactt cactcatccc tgcgaccatg aggagattcg tgagaacctg agtctcaaaa     600
atggctctgg ttttgggaaa aaaagcaaag acatgtccac agagcgggac ttcttcatga     660
ggatgaagtg cacggtcacc aacagaggcc gtactgtcaa cctcaagtca gccacctgga     720
aggtcttgca ctgcacgggc caggtgaaag tctacaacaa ctgccctcct cacaatagtc     780
tgtgtggcta caaggagccc ctgctgtcct gcctcatcat catgtgtgaa ccaatccagc     840
acccatccca catggacatc cccctggata gcaagacctt cctgagccgc acagcatgg     900 acatgaagtt cacctactgt gatgacagaa tcacagaact gattggttac caccctgagg     960
agctgcttgg ccgctcagcc tatgaattct accatgcgct agactccgag aacatgacca    1020
agagtcacca gaacttgtgc accaagggtc aggtagtaag tggccagtac cggatgctcg    1080
caaagcatgg gggctacgtg tggctggaga cccaggggac ggtcatctac aaccctcgca    1140
```

```
acctgcagcc ccagtgcatc atgtgtgtca actacgtcct gagtgagatt gagaagaatg    1200
acgtggtgtt ctccatggac cagactgaat ccctgttcaa gccccacctg atggccatga    1260
acagcatctt tgatagcagt ggcaaggggg ctgtgtctga aagagtaac ttcctattca     1320 ccaagctaaa ggaggagccc gaggagctgg cccagctggc tcccacccca ggagacgcca    1380
tcatctctct ggatttcggg aatcagaact tcgaggagtc ctcagcctat ggcaaggca    1440 tcctgccccc gagccagcca tgggccacgg agttgaggag ccacagcacc cagagcgagg   1500
ctgggagcct gcctgccttc accgtgcccc aggcagctgc cccgggcagc accaccccca   1560
gtgccaccag cagcagcagc agctgctcca cgcccaatag ccctgaagac tattacacat   1620
ctttggataa cgacctgaag attgaagtga ttgagaagct cttcgccatg gacacagagg   1680
ccaaggacca atgcagtacc cagacggatt tcaatgagct ggacttggag acgctagcag   1740
cctatatccc catggacggg gaagacttcc agctaagccc catctgcccc gaggagcggc   1800
tcttggcgga gaacccacag tccaccccca gcactgctt cagtgccatg acaaacatct    1860
tccagccact ggcccctgta gccccgcaca gtcccttcct cctggacaag tttcagcagc   1920
agctggagag caagaagaca gagcccgagc accggcccat gtcctccatc ttctttgatg   1980
ccggaagcaa agcatccctg ccaccgtgct gtggccaggc cagcacccct ctctcttcca   2040 tgggggggcag atccaatacc cagtggcccc cagatccacc attacatttt gggcccacaa   2100
agtgggccgt cggggatcag cgcacagagt tcttgggagc agcgccgttg gggcccctg    2160 tctctccacc ccatgtctcc accttcaaga caaggtctgc aaagggtttt ggggcacgag   2220
gcccagacgt gctgagtccg gccatggtag ccctctccaa caagctgaag ctgaagcgac   2280
agctggagta tgaagagcaa gccttccagg acctgagcgg gggggaccca cctggtggca   2340
gcacctcaca tttgatgtgg aaacggatga agaacctcag gggtgggagc tgcccttga    2400 tgccggacaa gccactgagc gcaaatgtac caatgataa gttcacccaa aaccccatga    2460
ggggcctggg ccatcccctg agacatctgc cgctgccaca gcctccatct gccatcagtc   2520
ccggggagaa cagcaagagc aggttccccc cacagtgcta cgccacccag taccaggact   2580
acagcctgtc gtcagcccac aaggtgtcag gcatggcaag ccggctgctc gggccctcat   2640
ttgagtccta cctgctgccc gaactgacca gatatgactg tgaggtggcg gtacccgtgc   2700
tgggaagctc cacgctcctg caaggagggg acctcctcag agccctggac caggccacct   2760
ga                                                                 2762
```

<210> SEQ ID NO 3
<211> LENGTH: 869
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 3

Met Thr Ala Asp Lys Glu Lys Arg Ser Ser Glu Arg Arg Lys
1               5                   10                  15

Glu Lys Ser Arg Asp Ala Ala Arg Cys Arg Arg Ser Lys Glu Thr Glu
                20                  25                  30

Val Phe Tyr Glu Leu Ala His Glu Leu Pro Leu Pro His Ser Val Ser
            35                  40                  45

Ser His Leu Asp Lys Ala Ser Ile Met Arg Leu Ala Ile Ser Phe Leu
        50                  55                  60

```
Arg Thr His Lys Leu Leu Ser Ser Val Cys Ser Glu Asn Glu Ser Glu
 65                  70                  75                  80

Ala Glu Ala Asp Gln Gln Met Asp Asn Leu Tyr Leu Lys Ala Leu Glu
             85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
            115                 120                 125

His Ser Ile Phe Asp Phe Thr His Pro Cys Asp His Glu Glu Ile Arg
            130                 135                 140

Glu Asn Leu Ser Leu Lys Asn Gly Ser Gly Phe Gly Lys Lys Ser Lys
145                 150                 155                 160

Asp Met Ser Thr Glu Arg Asp Phe Phe Met Arg Met Lys Cys Thr Val
            165                 170                 175

Thr Asn Arg Gly Arg Thr Val Asn Leu Lys Ser Ala Thr Trp Lys Val
            180                 185                 190

Leu His Cys Thr Gly Gln Val Lys Val Tyr Asn Asn Cys Pro Pro His
            195                 200                 205

Asn Ser Leu Cys Gly Tyr Lys Glu Pro Leu Leu Ser Cys Leu Ile Ile
210                 215                 220

Met Cys Glu Pro Ile Gln His Pro Ser His Met Asp Ile Pro Leu Asp
225                 230                 235                 240

Ser Lys Thr Phe Leu Ser Arg His Ser Met Asp Met Lys Phe Thr Tyr
            245                 250                 255

Cys Asp Asp Arg Ile Thr Glu Leu Ile Gly Tyr His Pro Glu Glu Leu
            260                 265                 270

Leu Gly Arg Ser Ala Tyr Glu Phe Tyr His Ala Leu Asp Ser Glu Asn
            275                 280                 285

Met Thr Lys Ser His Gln Asn Leu Cys Thr Lys Gly Gln Val Val Ser
            290                 295                 300

Gly Gln Tyr Arg Met Leu Ala Lys His Gly Gly Tyr Val Trp Leu Glu
305                 310                 315                 320

Thr Gln Gly Thr Val Ile Tyr Asn Pro Arg Asn Leu Gln Pro Gln Cys
            325                 330                 335

Ile Met Cys Val Asn Tyr Val Leu Ser Glu Ile Glu Lys Asn Asp Val
            340                 345                 350

Val Phe Ser Met Asp Gln Thr Glu Ser Leu Phe Lys Pro His Leu Met
            355                 360                 365

Ala Met Asn Ser Ile Phe Asp Ser Ser Gly Lys Gly Ala Val Ser Glu
            370                 375                 380

Lys Ser Asn Phe Leu Phe Thr Lys Leu Lys Glu Glu Pro Glu Glu Leu
385                 390                 395                 400

Ala Gln Leu Ala Pro Thr Pro Gly Asp Ala Ile Ile Ser Leu Asp Phe
            405                 410                 415

Gly Asn Gln Asn Phe Glu Glu Ser Ser Ala Tyr Gly Lys Ala Ile Leu
            420                 425                 430

Pro Pro Ser Gln Pro Trp Ala Thr Glu Leu Arg Ser His Ser Thr Gln
            435                 440                 445

Ser Glu Ala Gly Ser Leu Pro Ala Phe Thr Val Pro Gln Ala Ala Ala
            450                 455                 460

Pro Gly Ser Thr Thr Pro Ser Ala Thr Ser Ser Ser Ser Cys Ser
465                 470                 475                 480
```

```
Thr Pro Asn Ser Pro Glu Asp Tyr Tyr Thr Ser Leu Asp Asn Asp Leu
                485                 490                 495
Lys Ile Glu Val Ile Glu Lys Leu Phe Ala Met Asp Thr Glu Ala Lys
            500                 505                 510
Asp Gln Cys Ser Thr Gln Thr Asp Phe Asn Glu Leu Asp Leu Glu Thr
        515                 520                 525
Leu Ala Ala Tyr Ile Pro Met Asp Gly Glu Asp Phe Gln Leu Ser Pro
    530                 535                 540
Ile Cys Pro Glu Glu Arg Leu Leu Ala Glu Asn Pro Gln Ser Thr Pro
545                 550                 555                 560
Gln His Cys Phe Ser Ala Met Thr Asn Ile Phe Gln Pro Leu Ala Pro
                565                 570                 575
Val Ala Pro His Ser Pro Phe Leu Leu Asp Lys Phe Gln Gln Gln Leu
            580                 585                 590
Glu Ser Lys Lys Thr Glu Pro Glu His Arg Pro Met Ser Ser Ile Phe
        595                 600                 605
Phe Asp Ala Gly Ser Lys Ala Ser Leu Pro Pro Cys Cys Gly Gln Ala
    610                 615                 620
Ser Thr Pro Leu Ser Ser Met Gly Gly Arg Ser Asn Thr Gln Trp Pro
625                 630                 635                 640
Pro Asp Pro Pro Leu His Phe Gly Pro Thr Lys Trp Ala Val Gly Asp
                645                 650                 655
Gln Arg Thr Glu Phe Leu Gly Ala Ala Pro Leu Gly Pro Pro Val Ser
            660                 665                 670
Pro Pro His Val Ser Thr Phe Lys Thr Arg Ser Ala Lys Gly Phe Gly
        675                 680                 685
Ala Arg Gly Pro Asp Val Leu Ser Pro Ala Met Ala Leu Ser Asn Lys
    690                 695                 700
Leu Lys Leu Lys Arg Gln Leu Glu Tyr Glu Glu Gln Ala Phe Gln Asp
705                 710                 715                 720
Leu Ser Gly Gly Asp Pro Pro Gly Gly Ser Thr Ser His Leu Met Trp
                725                 730                 735
Lys Arg Met Lys Asn Leu Arg Gly Gly Ser Cys Pro Leu Met Pro Asp
            740                 745                 750
Lys Pro Leu Ser Ala Asn Val Pro Asn Asp Lys Phe Thr Gln Asn Pro
        755                 760                 765
Met Arg Gly Leu Gly His Pro Leu Arg His Leu Pro Leu Pro Gln Pro
    770                 775                 780
Pro Ser Ala Ile Ser Pro Gly Glu Asn Ser Lys Ser Arg Phe Pro Pro
785                 790                 795                 800
Gln Cys Tyr Ala Thr Gln Tyr Gln Asp Tyr Ser Leu Ser Ser Ala His
                805                 810                 815
Lys Val Ser Gly Met Ala Ser Arg Leu Leu Gly Pro Ser Phe Glu Ser
            820                 825                 830
Tyr Leu Leu Pro Glu Leu Thr Arg Tyr Asp Cys Glu Val Ala Val Pro
        835                 840                 845
Val Leu Gly Ser Ser Thr Leu Leu Gln Gly Gly Asp Leu Leu Arg Ala
    850                 855                 860
Leu Asp Gln Ala Thr
865

<210> SEQ ID NO 4
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 4
gagttctctg ctgcctcctg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agctctaatg cgctgttaat                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccaccccat gtctccacct                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccatgcctg acaccttgtg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttgatgtgga aacggatgaa                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaacctgct cttgctgttc                                              20

<210> SEQ ID NO 10
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 10
caccacagtc catgccatca ct                                            22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tccaccaccc tgttgctgta g                                             21
```